United States Patent
Mochizuki

(10) Patent No.: US 10,471,200 B2
(45) Date of Patent: Nov. 12, 2019

(54) BLOOD PURIFICATION APPARATUS

(71) Applicant: Nikkiso Company Limited, Tokyo (JP)

(72) Inventor: Hiroaki Mochizuki, Shizuoka (JP)

(73) Assignee: Nikkiso Company Limited, Tokyo (JP)

(*) Notice: Subject to any disclaimer, the term of this patent is extended or adjusted under 35 U.S.C. 154(b) by 241 days.

(21) Appl. No.: 15/458,219

(22) Filed: Mar. 14, 2017

(65) Prior Publication Data

US 2017/0182238 A1  Jun. 29, 2017

Related U.S. Application Data

(63) Continuation of application No. PCT/JP2015/076143, filed on Sep. 15, 2015.

(30) Foreign Application Priority Data

Sep. 16, 2014 (JP) .................................. 2014-187683

(51) Int. Cl.
  *A61M 1/34* (2006.01)
  *A61M 1/14* (2006.01)
  (Continued)

(52) U.S. Cl.
  CPC ............ *A61M 1/3413* (2013.01); *A61M 1/14* (2013.01); *A61M 1/16* (2013.01); *A61M 1/34* (2013.01);
  (Continued)

(58) Field of Classification Search
  None
  See application file for complete search history.

(56) References Cited

U.S. PATENT DOCUMENTS

2011/0098625 A1* 4/2011 Masala ................. A61M 1/342
                                                          604/6.09
2015/0283314 A1* 10/2015 Cho .................... A61M 1/1649
                                                          210/195.2

FOREIGN PATENT DOCUMENTS

JP   H10-263073 A   10/1998
JP   2001-112863 A   4/2001
(Continued)

OTHER PUBLICATIONS

Extended European Search Report, Application No. 15842843.3 dated Feb. 27, 2018.

*Primary Examiner* — Richard C Gurtowski
(74) *Attorney, Agent, or Firm* — Young Basile Hanlon & MacFarlane, P.C.

(57) ABSTRACT

A blood purification apparatus capable of achieving a simplified configuration and switching between hemodialysis treatment (HD), hemofiltration treatment (HF), and hemodiafiltration treatment (HDF) as well as selecting from pre-dilution, post-dilution and pre and post-dilution easily and smoothly. The blood purification apparatus includes: a valve means 3 that is capable of closing and opening a dialysate introduction line and a dialysate supply line L3 in any manner, and a control unit 5 that operates the valve means 3 to allow any treatment to be performed selected from hemodialysis treatment in which the dialysate supply line L3 is closed while the dialysate introduction line L1 is opened, hemofiltration treatment in which the dialysate supply line L3 is opened while the dialysate introduction line L1 is closed, and hemodiafiltration treatment in which hemodialysis and hemofiltration are performed concurrently by alternately closing and opening the dialysate introduction line L1 and the dialysate supply line L3.

20 Claims, 5 Drawing Sheets

(51) Int. Cl.
    *A61M 39/22*     (2006.01)
    *A61M 1/16*     (2006.01)

(52) U.S. Cl.
    CPC ........ *A61M 1/3431* (2014.02); *A61M 1/3434* (2014.02); *A61M 1/3437* (2014.02); *A61M 39/22* (2013.01); *A61M 2205/3334* (2013.01)

(56) References Cited

FOREIGN PATENT DOCUMENTS

| | | |
|---|---|---|
| JP | 2011-112863 A | 4/2001 |
| JP | 2001-190660 A | 7/2001 |
| JP | 2006-081648 A | 3/2006 |
| JP | 2013-255677 A | 12/2013 |
| WO | 2005/061026 A2 | 7/2005 |
| WO | 2009/144522 A1 | 12/2009 |
| WO | 2009/147478 A1 | 12/2009 |

\* cited by examiner

[Fig. 1]
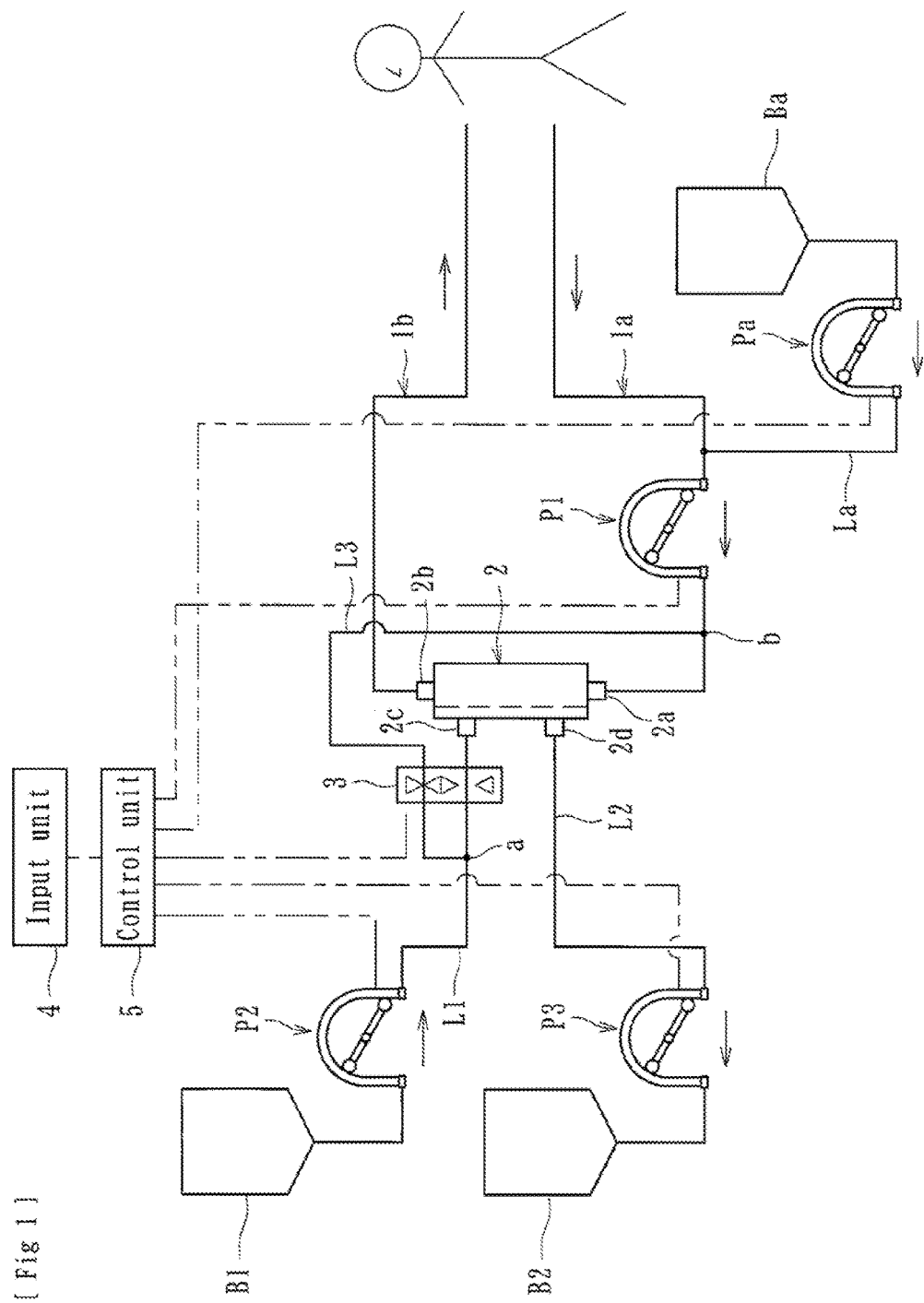

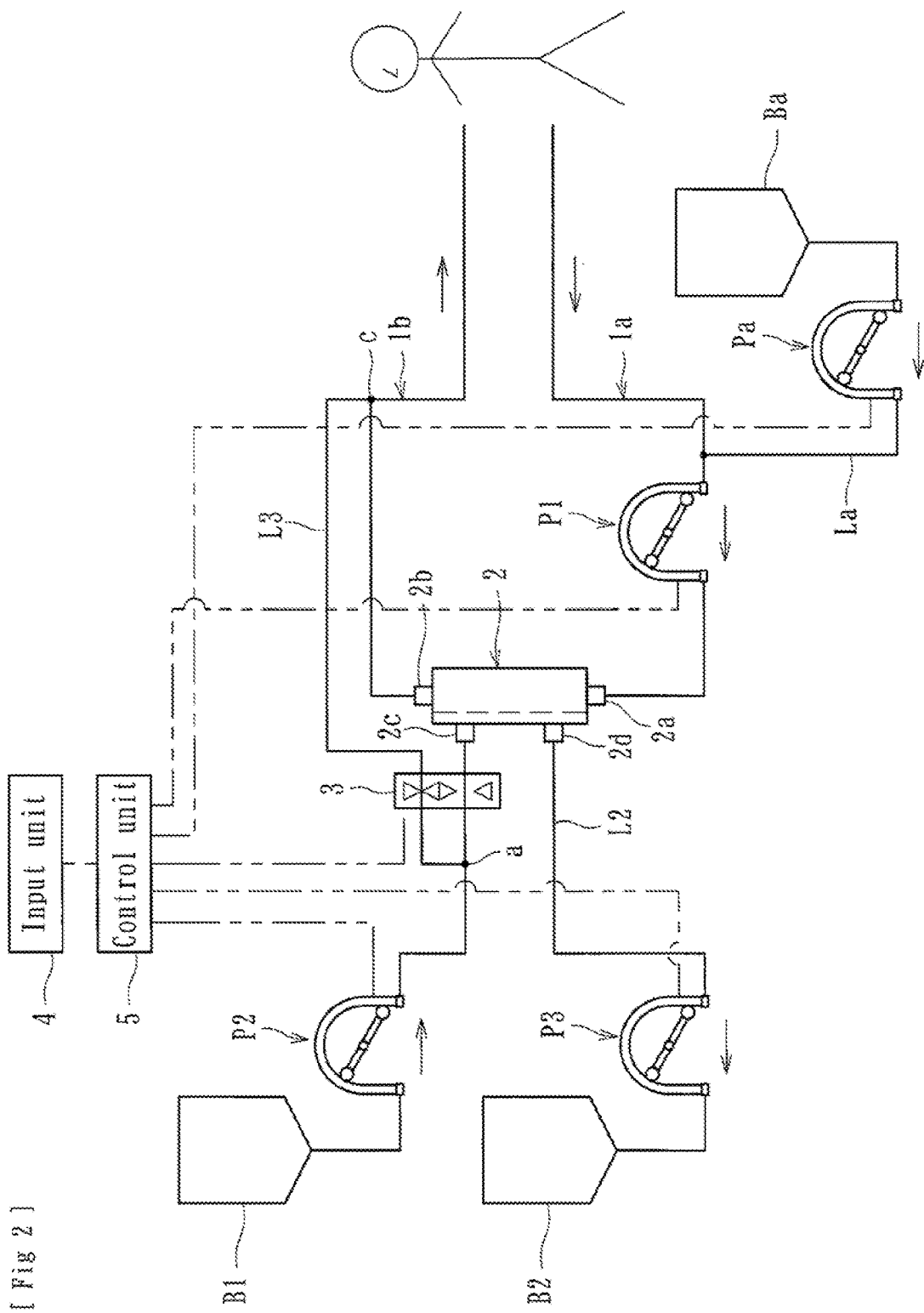
[Fig 2]

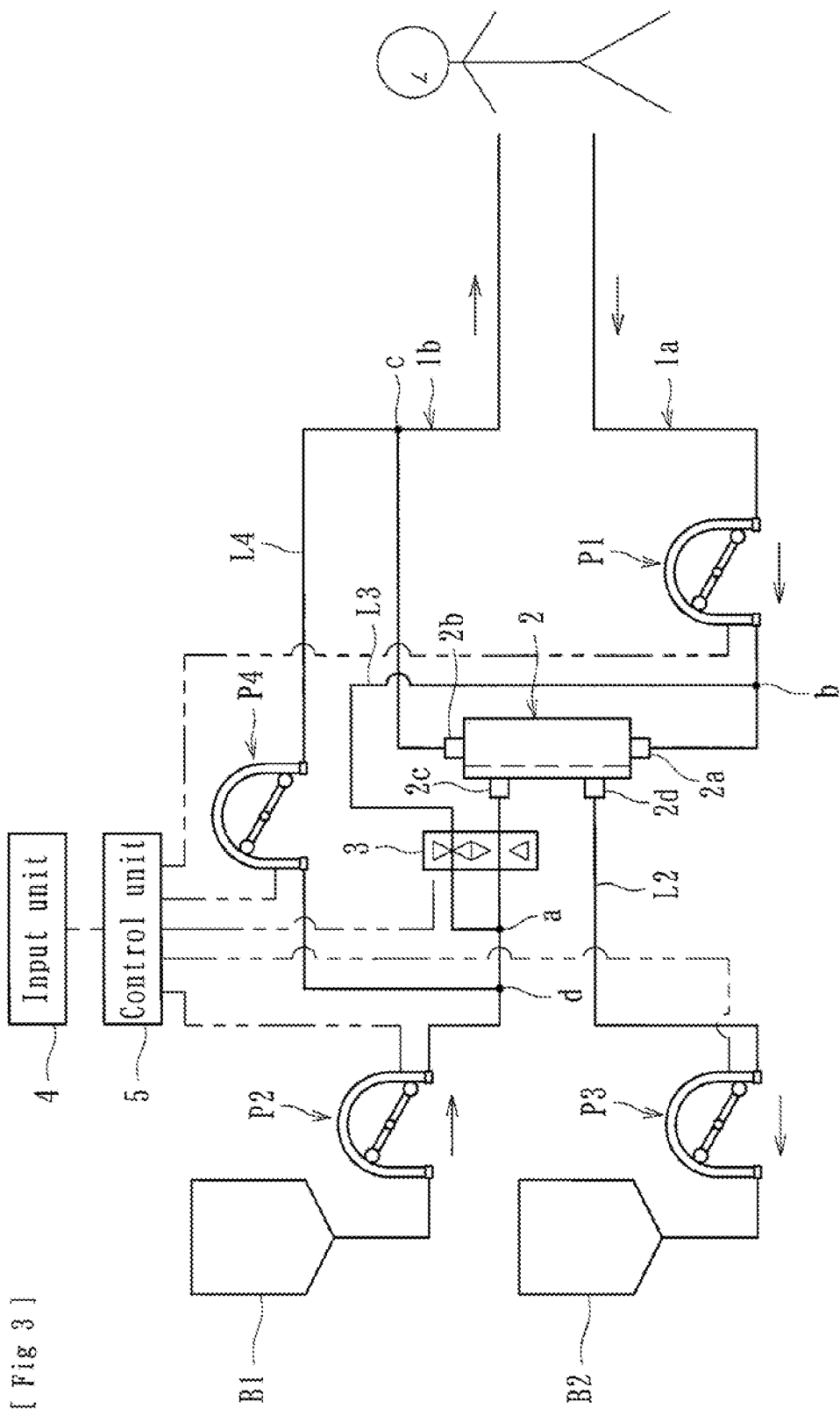
[Fig 3]

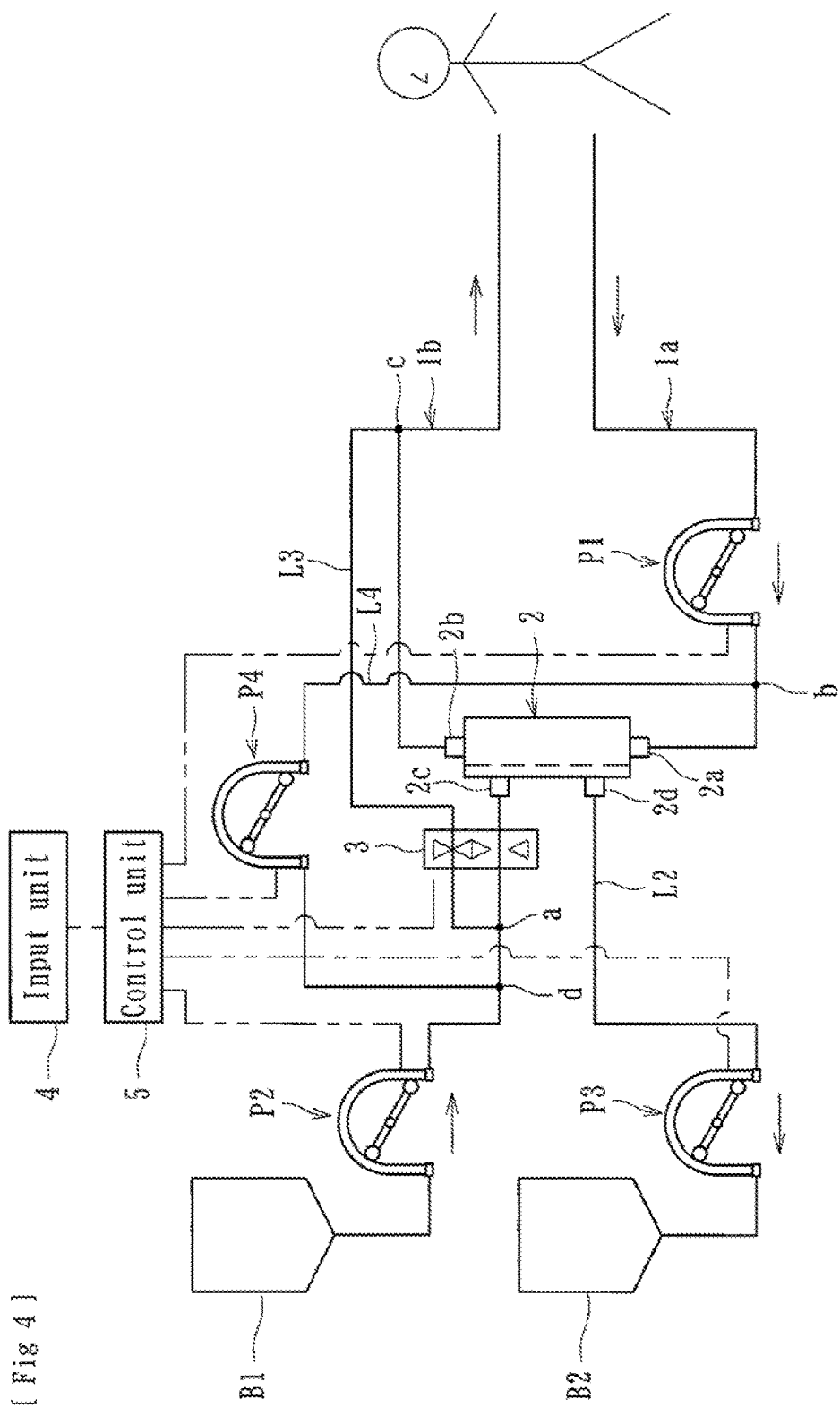
[Fig 4]

[Fig 5]
(a)
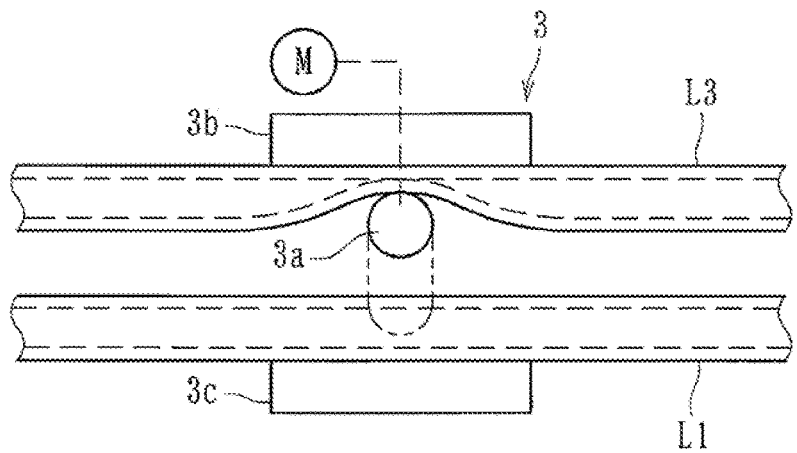
(b)
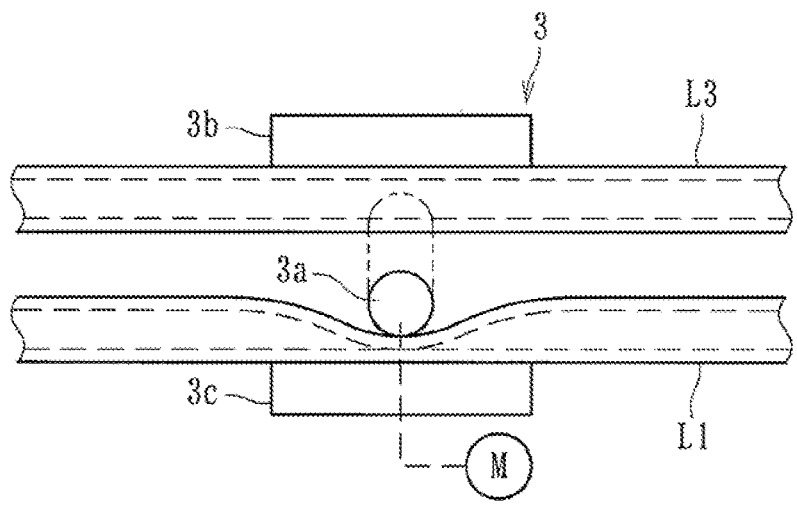
[Fig 6]
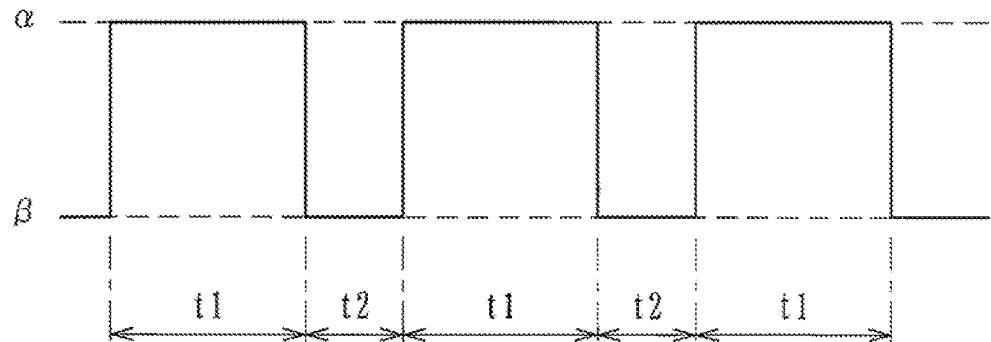

BLOOD PURIFICATION APPARATUS

FIELD

The present invention relates to a blood purification apparatus for extracorporeally circulating the blood of a patient to purify the blood.

BACKGROUND

In general, a blood purification apparatus for performing hemodialysis treatment includes an arterial blood circuit and a venous blood circuit that constitute a blood circuit for extracorporeally circulating the blood of a patient, a blood purifier for purifying the blood extracorporeally circulated by the blood circuit, and a device provided with various treatment means such as a blood pump for performing blood purification treatment by the blood circuit and the blood purifier. An arterial puncture needle and a venous puncture needle are attachable to the leading ends of the arterial blood circuit and the venous blood circuit.

After the arterial puncture needle and the venous puncture needle are inserted in a patient, a blood pump is driven, thereby causing the blood of a patient to flow in the arterial blood circuit and the venous blood circuit, and in the process of the flowing, blood purification is performed by the blood purifier. Also, in hemodialysis treatment, a dialysate introduction line for introducing dialysate into the blood purifier, and a dialysate discharge line for discharging dialysate from the blood purifier are each connected to the blood purifier.

In blood purification treatment, there are established treatments: hemodialysis treatment (HD) in which dialysate is caused to flow through a dialysate flow path of the blood purifier, and substances in the blood are thereby removed by a diffusion effect via a blood purification membrane; hemofiltration treatment (HF) in which water and substances in the blood are removed by an effect of ultrafiltration pressure in the blood purifier, and a substitution solution equivalent in amount to the removed water is injected into the blood; and hemodiafiltration (HDF) in which hemodialysis treatment (HD) and hemofiltration treatment (HF) are performed concurrently. Particularly when blood purification treatment is performed on a patient having a disorder such as acute renal failure, it is necessary to switch between and perform one of hemodialysis (HD), hemofiltration (HF) and hemodiafiltration (HDF) according to the conditions of the patient in a treatment process.

Also, in hemofiltration treatment (HF) and hemodiafiltration treatment (HDF), dilution is performed which is variously selected from: pre-dilution in which a substitution solution is injected into the upstream side (the arterial blood circuit) of the blood purifier; post-dilution in which a substitution solution is injected into the downstream side (the venous blood circuit) of the blood purifier; and pre and post-dilution in which a substitution solution is injected into both the upstream side and downstream side (the arterial blood circuit and the venous blood circuit). Thus, nowadays, a blood purification apparatus capable of switching between hemodialysis treatment (HD), hemofiltration treatment (HF), and hemodiafiltration treatment (HDF) and selecting any from pre-dilution, post-dilution, and pre and post-dilution is called for.

To cope with such needs, a blood purification apparatus has been proposed in the past that includes a plurality of dialysate supply lines branching from a dialysate introduction line and connected to a blood circuit, liquid delivery pumps and a plurality of electromagnetic valves disposed in each of the dialysate supply lines, the blood purification apparatus being capable of switching between hemodialysis treatment (HD), hemofiltration treatment (HF), and hemodiafiltration treatment (HDF) as well as selecting from pre-dilution, post-dilution and pre and post-dilution by connecting the leading end of each dialysate supply line to a predetermined portion of the blood circuit according to a treatment type then supplying the dialysate of the dialysate introduction line to the blood circuit as a substitution solution. It is to be noted that such prior art is not related to an invention with publicly known literature, thus there is no information on prior art literature to be cited.

SUMMARY

However, the above-described conventional blood purification apparatus have problems in that a great number of flow paths, liquid delivery pumps and electromagnetic valves for opening and closing the flow paths are needed in order to supply dialysate to the blood circuit, which results in a complicated configuration of the apparatus, and work of connecting a dialysate supply line is necessary according to a treatment type, which results in a troublesome work. Particularly, when the dialysate of the dialysate introduction line is delivered to the blood circuit, the flow rate of the dialysate needs to be controlled to a desired rate by a liquid delivery pump disposed in a flow path, and thus the same number of liquid delivery pumps and valve means as the number of dialysate supply lines are necessary, which results in a problem that the configuration is more complicated.

The present teachings have been made in view of such a situation, and aims to provide a blood purification apparatus capable of achieving a simplified configuration and switching between hemodialysis treatment (HD), hemofiltration treatment (HF), and hemodiafiltration treatment (HDF) as well as selecting from pre-dilution and post-dilution easily and smoothly.

The present teachings provide a blood purification apparatus comprising: a blood circuit that includes an arterial blood circuit and a venous blood circuit, and that is capable of extracorporeally circulating blood of a patient from a leading end of the arterial blood circuit to a leading end of the venous blood circuit; a blood purification means that is interposed between the arterial blood circuit and the venous blood circuit of the blood circuit, and that is capable of purifying blood that flows through the blood circuit; a blood pump disposed in the arterial blood circuit; a dialysate introduction line for introducing dialysate to the blood purification means, and a dialysate discharge line for discharging the dialysate from the blood purification means; a liquid delivery pump disposed in the dialysate introduction line; and a dialysate supply line that branches from a downstream side of the liquid delivery pump in the dialysate introduction line and is connected to a predetermined portion of the blood circuit, and that is capable of supplying the dialysate of the dialysate introduction line to the blood circuit, wherein the blood purification apparatus includes a valve means that is capable of closing and opening the dialysate introduction line and the dialysate supply line in any manner, and a control unit that operates the valve means to allow any treatment to be performed selected from hemodialysis treatment in which the dialysate supply line is closed while the dialysate introduction line is opened, hemofiltration treatment in which the dialysate supply line is opened while the dialysate introduction line is closed, and hemodiafiltration treatment in which hemodialysis and hemofiltration are performed concurrently (together in the same process) by alternately closing and opening the dialysate introduction line and the dialysate supply line.

The present teachings provide the blood purification apparatus according to the teachings herein, wherein the valve means has a single movable unit that is disposed to straddle the dialysate introduction line and the dialysate supply line, and the movable unit is operable by an actuator to close one of the dialysate introduction line and the dialysate supply line and open the other as well as to close the other and open the one.

The present teachings provide the blood purification apparatus according to the teachings herein, wherein when the hemodiafiltration treatment is selected, the valve means is capable of setting a time during which one of the dialysate introduction line and the dialysate supply line is closed and the other is opened, and a time during which the other is closed and the one is opened in any manner.

The present teachings provide the blood purification apparatus according to the teachings herein, further comprising a second dialysate supply line that branches from an upstream side of a branch point of the dialysate supply line in the dialysate introduction line and is connected to the blood circuit, and a liquid delivery pump is disposed at a midpoint of the second dialysate supply line, wherein the second dialysate supply line and the dialysate supply line are connected to each of the arterial blood circuit and the venous blood circuit.

The present teachings provide the blood purification apparatus according to the teachings herein, wherein the liquid delivery pump is comprised of a peristaltic pump that delivers liquid by pressing and rubbing against a flexible tube that forms a flow path.

According to the present teachings, the blood purification apparatus includes a valve means and a control unit, and thus the apparatus configuration can be simplified and switching between hemodialysis treatment (HD), hemofiltration treatment (HF), and hemodiafiltration treatment (HDF) in which hemodialysis and hemofiltration can be performed concurrently, as well as selecting from pre-dilution and post-dilution can be performed easily and smoothly.

According to the present teachings, the valve means has a single movable unit that is disposed to straddle the dialysate introduction line and the dialysate supply line, and the movable unit is operable by an actuator to close one of the dialysate introduction line and the dialysate supply line and open the other as well as to close the other and open the one. Thus, the apparatus configuration can be more simplified.

According to the teachings herein, when the hemodiafiltration treatment is selected, the valve means is capable of setting a time during which one of the dialysate introduction line and the dialysate supply line is closed and the other is opened, and a time during which the other is closed and the one is opened in any manner. Thus, hemodiafiltration treatment (HDF) according to the conditions of the patient and the apparatus configuration can be performed.

According to the teachings herein, the blood purification apparatus comprises a second dialysate supply line that branches from an upstream side of a branch point of the dialysate supply line in the dialysate introduction line and is connected to the blood circuit, and a liquid delivery pump is disposed at a midpoint of the second dialysate supply line, wherein the second dialysate supply line and the dialysate supply line are connected to each of the arterial blood circuit and the venous blood circuit. Thus, selection from pre-dilution, post-dilution and pre and post-dilution in hemofiltration treatment (HF) and hemodiafiltration treatment (HDF) can be performed more easily and smoothly.

According to the teachings herein, the liquid delivery pump is comprised of a peristaltic pump that delivers liquid by pressing and rubbing against a flexible tube that forms a flow path. Thus, a desired amount of liquid delivery can be made with high accuracy and when the pump is stopped, the flow of liquid can be blocked by closing the flow path.

BRIEF DESCRIPTION OF THE DRAWINGS

FIG. 1 is a schematic diagram illustrating a blood purification apparatus (post-dilution) according to a first embodiment of the present invention.

FIG. 2 is a schematic diagram illustrating the blood purification apparatus (pre-dilution).

FIG. 3 is a schematic diagram illustrating a blood purification apparatus according to a second embodiment of the present invention.

FIG. 4 is a schematic diagram illustrating a blood purification apparatus according to a third embodiment of the present invention.

FIG. 5 is a schematic diagram illustrating a valve means applied to an embodiment of the present invention.

FIG. 6 is a timing diagram illustrating the operation timing of the valve means.

DETAILED DESCRIPTION

Hereinafter, an embodiment of the present invention will be specifically described with reference to the drawings. A blood purification apparatus according to a first embodiment is applied to a hemodialysis apparatus for extracorporeally circulating the blood of a patient to purify the blood. As illustrated in FIGS. 1 and 2, the blood purification apparatus mainly comprises: a blood circuit including an arterial blood circuit 1a and a venous blood circuit 1b; a dialyzer 2 (blood purification means) that is interposed between the arterial blood circuit 1a and the venous blood circuit 1b, and that purifies the blood which flows through the blood circuit; a blood pump P1 comprised of a peristaltic pump disposed in the arterial blood circuit 1a; a dialysate introduction line L1 and a dialysate discharge line L2; liquid delivery pumps P2, P3 respectively disposed in the dialysate introduction line L1 and the dialysate discharge line L2; a dialysate supply line L3; an input unit 4; and a control unit 5.

A connector is connected to the leading end of each of the arterial blood circuit 1a and the venous blood circuit 1b, and an arterial puncture needle and a venous puncture needle (not illustrated) can be coupled via the connector. When the blood pump P1 is driven (forward rotation drive) in a state where the arterial puncture needle coupled to the leading end of the arterial blood circuit 1a and the venous puncture needle coupled to the leading end of the venous blood circuit 1b are inserted into a patient, the blood of the patient reaches the dialyzer 2 through the arterial blood circuit 1a, and after blood purification is performed by the dialyzer 2, the blood returns to the body of the patient through the venous blood circuit 1b. Thus, the blood of the patient can be purified by the dialyzer 2 while being extracorporeally circulated from the leading end of the arterial blood circuit 1a of the blood circuit to the leading end of the venous blood circuit 1b. It is to be noted that either approach may be used: the arterial puncture needle and the venous puncture needle are inserted into the subclavian vein or the femoral vein of the patient with a double lumen catheter or inserted into an arm of the patient.

In the case body of the dialyzer 2, a blood inlet hole 2a (blood inlet port), a blood outlet hole 2b (blood outlet port), a dialysate inlet hole 2c (dialysate flow path entry: dialysate inlet port) and a dialysate outlet hole 2d (dialysate flow path exit: dialysate outlet port) are formed. Among these, the blood inlet hole 2a is connected to the base end of the arterial blood circuit 1a, and the blood outlet hole 2b is connected to the base end of the venous blood circuit 1b. Also, the dialysate inlet hole 2c and the dialysate outlet hole 2d are connected to the dialysate introduction line L1 and the dialysate discharge line L2, respectively.

A plurality of hollow fiber membranes (not illustrated) is housed in the dialyzer 2, and the hollow fiber forms blood purification membranes for purifying blood. In such dialyzer 2, there are formed a blood flow path (flow path between the blood inlet hole 2a and the blood outlet hole 2b) through which the blood of the patient flows via the blood purification membranes, and a dialysate flow path (flow path between the dialysate inlet hole 2c and the dialysate outlet hole 2d) through which dialysate flows. In the hollow fiber membranes forming the blood purification membranes, a great number of fine holes (bores) through the outer circumferential surface and the inner circumferential surface is formed to form the hollow fiber membranes, via which impurities in the blood can permeate into the dialysate.

One end of the dialysate introduction line L1 is connected to the dialysate inlet hole 2c of the dialyzer 2, and in the dialysate introduction line L1, there is disposed the liquid delivery pump P2 comprised of a peristaltic pump that delivers liquid by pressing and rubbing against a flexible tube that forms the flow path of the dialysate introduction line L1. The other end of the dialysate introduction line L1 is connected to a storage bag B1 in which a predetermined amount of dialysate is stored, and the dialysate in the storage bag B1 can be introduced into the dialyzer 2 by driving the liquid delivery pump P2.

One end of the dialysate discharge line L2 is connected to the dialysate outlet hole 2d of the dialyzer 2, and in the dialysate discharge line L2, there is disposed the liquid delivery pump P3 comprised of a peristaltic pump that delivers liquid by pressing and rubbing against a flexible tube that forms the flow path of the dialysate discharge line L2. The other end of the dialysate discharge line L2 is connected to a storage bag B2 in which a predetermined amount of dialysate can be stored, and the dialysate (discharged liquid) discharged from the dialyzer 2 can be introduced into the storage bag B2 by driving the liquid delivery pump P3.

Thus, driving the liquid delivery pump P2 causes the dialysate of the storage bag B1 to flow toward the dialyzer 2, and driving the liquid delivery pump P3 causes the dialysate (discharged liquid) of the dialyzer 2 to flow toward the storage bag B2. It is to be noted that the storage bags B1, B2 are hooked by respective hooks (not illustrated) disposed in the dialysis device body, and are configured to measure a weight in real time by a weight scale which is not illustrated. Thus, it is possible to supply dialysate to the dialyzer 2 and to discharge the dialysate from the dialyzer 2 at a set flow rate.

It is to be noted that the arterial blood circuit 1a is connected to a flow path La in which a liquid delivery pump Pa comprised of a peristaltic pump is disposed, and the leading end of the flow path La is connected to the storage bag Ba. In the storage bag Ba, for instance, pharmacological agent such as anticoagulant is stored, and the pharmacological agent and the like can be injected to the blood extracorporeally circulating through the arterial blood circuit 1a and the venous blood circuit 1b by driving the liquid delivery pump Pa.

The dialysate supply line L3 branches from the downstream side (side of the dialyzer 2) of the liquid delivery pump P2 in the dialysate introduction line L1 and is connected to a predetermined portion of the blood circuit, and the dialysate supply line L3 is comprised of a flow path capable of supplying the dialysate of the dialysate introduction line L1 to the blood circuit. It is to be noted that the leading end of the dialysate supply line L3 according to this embodiment is selectively connectable to a connecting portion b (between the disposition position of the blood pump P1 and the dialyzer 2) of the arterial blood circuit and a connecting portion c of the venous blood circuit, and connection to the connecting portion b allows pre-dilution as well as connection to the connecting portion c allows post-dilution.

Here, in this embodiment, a valve means 3 is disposed that is capable of closing and opening the dialysate introduction line L1 and the dialysate supply line L3 in any manner. As illustrated in FIG. 5, the valve means 3 has a single movable unit 3a that is disposed to straddle the dialysate introduction line L1 (a portion on the downstream side from a branch point a of the dialysate supply line L3 and between the branch point a and the dialyzer 2) and the dialysate supply line L3, and the movable unit 3a is operable by a motor M (actuator) to close one of the dialysate introduction line L1 and the dialysate supply line L3 and open the other as well as to close the other and open the one.

More specifically, the valve means 3 includes the movable unit 3a that is reciprocatable by the motor M, one wall portion 3b and the other wall portion 3c. The valve means 3 is configured such that the dialysate supply line L3 is disposed, for instance, between the movable unit 3a and the one wall portion 3b, and the dialysate introduction line L1 is disposed between the movable unit 3a and the other wall portion 3c. When the motor M is driven to operate the valve means 3, the movable unit 3a closes the dialysate supply line L3 and opens the dialysate introduction line L1 (see (a) of FIG. 5), then the movable unit 3a moves and closes the dialysate introduction line L1 and opens the dialysate supply line L3 (see (b) of FIG. 5).

The input unit 4 allows input to a hemodialysis apparatus by a medical professional such as a doctor, and it is possible to input a desired treatment out of hemodialysis treatment (HD) in which dialysate is caused to flow through a dialysate flow path of the dialyzer 2 (blood purifier), and substances in the blood are thereby removed by a diffusion effect via a blood purification membrane; hemofiltration treatment (HF) in which water and substances in the blood are removed by an effect of ultrafiltration pressure in the dialyzer 2, and a substitution solution equivalent in amount to the removed water is injected into the blood; and hemodiafiltration treatment (HDF) in which hemodialysis treatment (HD) and hemofiltration treatment (HF) are performed concurrently.

The control unit 5 is electrically connected to the blood pump P1, the liquid delivery pumps P2, P3, and the valve means 3 to cause a treatment inputted by the input unit 4 to be performed. The control unit 5 is configured to operate the valve means to allow any treatment to be performed selected from hemodialysis treatment in which the dialysate supply line L3 is closed while the dialysate introduction line L1 is opened, hemofiltration treatment in which the dialysate supply line L3 is opened while the dialysate introduction line L1 is closed, and hemodiafiltration treatment in which hemodialysis and hemofiltration are performed concurrently by alternately closing and opening the dialysate introduction line L1 and the dialysate supply line L3.

When hemodialysis treatment is selected, as illustrated in (a) of FIG. 5, the control unit 5 allows the movable unit 3a of the valve means 3 to cause the dialysate supply line L3 to assume a closed state and the dialysate introduction line L1 to assume an opened state, and drives each of the blood pump P1, the liquid delivery pumps P2, P3. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the dialyzer 2, and thus hemodialysis treatment is performed.

When hemofiltration treatment is selected, as illustrated in (b) of FIG. 5, the control unit 5 allows the movable unit 3a of the valve means 3 to cause the dialysate introduction line L1 to assume a closed state and the dialysate supply line L3 to assume an opened state, and drives each of the blood pump P1, the liquid delivery pumps P2, P3. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the blood circuit (the arterial blood circuit 1a in the connected state of FIG. 1, the venous blood circuit 1b in the connected state of FIG. 2), and thus hemofiltration treatment is performed. It is to be noted that pre-dilution is performed in the connected state of FIG. 1, and post-dilution is performed in the connected state of FIG. 2.

When hemodiafiltration treatment is selected, the control unit 5 alternately achieves the state of (a) of FIG. 5 and the state of (b) of FIG. 5 (switches between closing and opening at a predetermined period), and drives each of the blood pump P1, the liquid delivery pumps P2, P3. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the dialyzer 2 and the blood circuit (the arterial blood circuit 1a in the connected state of FIG. 1, the venous blood circuit 1b in the connected state of FIG. 2), and thus hemodiafiltration treatment is performed in which hemodialysis (diffusion) and hemofiltration are performed concurrently. It is sufficient that the hemodiafiltration treatment according to the present invention be a treatment in which hemodialysis (diffusion) and hemofiltration are performed concurrently (together in the same process). It is to be noted that pre-dilution is performed in the connected state of FIG. 1, and post-dilution is performed in the connected state of FIG. 2.

When hemodiafiltration treatment is selected, as illustrated in FIG. 6, the valve means 3 is preferably capable of setting a time t1 (time in α state) during which one of the dialysate introduction line L1 and the dialysate supply line L3 is closed and the other is opened, and a time t2 (time in β state) during which the other is closed and the one is opened in any manner. For instance, when the average flow rate of the dialysate supplied to the dialyzer 2 and the average flow rate of the dialysate supplied to the blood circuit are set to a:b, the valve means 3 is operated so that time t1 during which the dialysate supply line L3 is closed: time t2 during which the dialysate introduction line L1 is closed equals a:b.

According to the embodiment, the blood purification apparatus includes the valve means 3 and the control unit 5, and thus the apparatus configuration can be simplified and switching between hemodialysis treatment (HD), hemofiltration treatment (HF), and hemodiafiltration treatment (HDF) as well as selecting from pre-dilution, post-dilution and pre and post-dilution can be performed easily and smoothly. In particular, the valve means 3 according to this embodiment has the single movable unit 3a that is disposed to straddle the dialysate introduction line L1 and the dialysate supply line L3, and the movable unit 3a is operable by the motor M to close one of the dialysate introduction line L1 and the dialysate supply line L3 and open the other as well as to close the other and open the one. Thus, the apparatus configuration can be more simplified. It is to be noted that instead of the motor M, another actuator may be used that can operate the movable unit 3a.

Furthermore, when hemodiafiltration treatment is selected, the valve means 3 according to this embodiment is capable of setting a time during which one of the dialysate introduction line and the dialysate supply line is closed and the other is opened, and a time during which the other is closed and the one is opened in any manner. Thus, hemodiafiltration treatment (HDF) according to the conditions of the patient and the apparatus configuration can be performed. Also, since the liquid delivery pumps P2, P3 (as well as the blood pump P1) applied to this embodiment are comprised of a peristaltic pump that delivers liquid by pressing and rubbing against a flexible tube that forms a flow path, a desired amount of liquid delivery can be made with high accuracy and when the pump is stopped, the flow of liquid can be blocked by closing the flow path.

Next, a second embodiment according to the present invention will be described. Similarly to the first embodiment, a blood purification apparatus according to this embodiment is applied to a hemodialysis apparatus for extracorporeally circulating the blood of a patient to purify the blood, and as illustrated in FIG. 3, the blood purification apparatus mainly comprises: a blood circuit including an arterial blood circuit 1a and a venous blood circuit 1b; a dialyzer 2 (blood purification means) that is interposed between the arterial blood circuit 1a and the venous blood circuit 1b, and that purifies the blood which flows through the blood circuit; a blood pump P1 comprised of a peristaltic pump disposed in the arterial blood circuit 1a; a dialysate introduction line L1 and a dialysate discharge line L2; liquid delivery pumps P2, P3 respectively disposed in the dialysate introduction line L1 and the dialysate discharge line L2; a dialysate supply line L3 connected to a connecting portion b of the arterial blood circuit 1a; a second dialysate supply line L4 in which a liquid delivery pump P4 is disposed at a midpoint; an input unit 4; and a control unit 5. It is to be noted that the same component as in the first embodiment is labeled with the same symbol, and a detailed description thereof is omitted.

The second dialysate supply line L4 branches from the upstream side (branch point d) of the branch point a of the dialysate supply line L3 in the dialysate introduction line L1 and is connected to the blood circuit (the connecting portion c of the venous blood circuit 1b), and the second dialysate supply line L4 is comprised of a flow path in which the liquid delivery pump P4 is disposed at a midpoint. Similarly to the liquid delivery pumps P2, P3 (as well as the blood pump P1), the liquid delivery pump P4 is comprised of a peristaltic pump that delivers liquid by pressing and rubbing against a flexible tube that forms the flow path of the second dialysate supply line L4.

Thus, the dialysate supply line L3 is connected to the connecting portion b of the arterial blood circuit 1a, and the second dialysate supply line L4 is connected to the connecting portion c of the venous blood circuit 1b, and thus the dialysate in the storage bag B1 can be supplied to the arterial blood circuit 1a (in other words, pre-dilution is possible) via the dialysate supply line L3 and can be supplied to the venous blood circuit 1b (in other words, post-dilution is possible) via the second dialysate supply line L4.

Similarly to the first embodiment, the input unit 4 allows input to a hemodialysis apparatus by a medical professional such as a doctor, and it is possible to input a desired treatment out of hemodialysis treatment (HD), hemofiltration treatment (HF) and hemodiafiltration treatment (HDF), and when hemofiltration treatment (HF) and hemodiafiltration treatment (HDF) are inputted, it is possible to select from pre-dilution in which dialysate (substitution solution) is injected into the upstream side (the arterial blood circuit 1a) of the dialyzer 2 (the blood purifier); post-dilution in which dialysate (substitution solution) is injected into the downstream side (the venous blood circuit 1b) of the dialyzer 2; and pre and post-dilution in which dialysate (substitution solution) is injected into both the upstream side and downstream side (the arterial blood circuit 1a and the venous blood circuit 1b) of the dialyzer 2.

The control unit 5 is electrically connected to the blood pump P1, the liquid delivery pumps P2, P3, P4 and the valve means 3 to cause a treatment inputted by the input unit 4 to be performed. The control unit 5 is configured to operate the valve means 3 to allow any treatment to be performed selected from hemodialysis treatment in which the dialysate supply line L3 is closed while the dialysate introduction line L1 is opened, hemofiltration treatment in which the dialysate supply line L3 is opened while the dialysate introduction line L1 is closed, and hemodiafiltration treatment in which the dialysate introduction line L1 and the dialysate supply line L3 are closed or opened in any manner.

When hemodialysis treatment is selected, as illustrated in (a) of FIG. 5, the control unit 5 allows the movable unit 3a of the valve means 3 to cause the dialysate supply line L3 to assume a closed state and the dialysate introduction line L1 to assume an opened state, and drives each of the blood pump P1, the liquid delivery pumps P2, P3. It is to be noted that the liquid delivery pump P4 is set to a stopped state. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the dialyzer 2, and thus hemodialysis treatment is performed.

When hemofiltration treatment is selected, as illustrated in (b) of FIG. 5, the control unit 5 allows the movable unit 3a of the valve means 3 to cause the dialysate introduction line L1 to assume a closed state and the dialysate supply line L3 to assume an opened state, and drives each of the blood pump P1, the liquid delivery pumps P2, P3. When pre-dilution is selected, the liquid delivery pump P4 is stopped and the liquid delivery pumps P2, P3 are driven. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the arterial blood circuit 1a, and thus hemofiltration treatment accompanied by pre-dilution is performed.

Also, in the case where hemofiltration treatment is selected, when post-dilution is selected, in addition to the blood pump P1 and the liquid delivery pumps P2, P3, the liquid delivery pump P4 is driven. At this point, when the flow rate due to driving of the liquid delivery pump P2 is Q1, the flow rate due to driving of the liquid delivery pump P4 is set to Q1, the flow rate due to driving of the liquid delivery pump P3 is set to Q1+Quf (where Q1>0, Quf≥0). With this, the dialysate in the storage bag B1 is introduced into the venous blood circuit 1b, and thus hemofiltration treatment accompanied by post-dilution is performed. It is to be noted that since an error may occur in the flow rates of the liquid delivery pumps P2, P4, the error can be absorbed by setting the flow rates of the liquid delivery pumps P2, P4 to be equal or setting the flow rate of the liquid delivery pump P4 to be smaller than the flow rate of the liquid delivery pump P2. In this case, an excessive amount flows through the arterial blood circuit 1a.

Furthermore, in the case where hemofiltration treatment is selected, when pre and post-dilution is selected, in addition to the blood pump P1 and the liquid delivery pumps P2, P3, the liquid delivery pump P4 is driven. At this point, when the flow rate due to driving of the liquid delivery pump P2 is Q1, the flow rate due to driving of the liquid delivery pump P4 is set to Q2 (where Q1>Q2>0), the flow rate due to driving of the liquid delivery pump P3 is set to Q1+Quf (where Q1>0, Quf≥0). With this, the dialysate in the storage bag B1 is introduced into the arterial blood circuit 1a and the venous blood circuit 1b, and thus hemofiltration treatment accompanied by pre and post-dilution is performed.

In the case where hemodiafiltration treatment is selected, when post-dilution is selected, as illustrated in (a) of FIG. 5, the control unit 5 allows the movable unit 3a of the valve means 3 to cause the dialysate supply line L3 to assume a closed state and the dialysate introduction line L1 to assume an opened state, and drives each of the blood pump P1, the liquid delivery pumps P2, P3, P4. At this point, when the flow rate due to driving of the liquid delivery pump P2 is Q1, the flow rate due to driving of the liquid delivery pump P4 is set to Q2 (where Q1>Q2>0), the flow rate due to driving of the liquid delivery pump P3 is set to Q1+Quf (where Q1>0, Quf≥0). With this, the dialysate in the storage bag B1 is introduced into the dialyzer 2 and the venous blood circuit 1b, and thus hemodiafiltration treatment accompanied by post-dilution is performed.

In the case where hemodiafiltration treatment is selected, when pre-dilution is selected, the control unit 5 alternately achieves the state of (a) of FIG. 5 and the state of (b) of FIG. 5 (switches between closing and opening at a predetermined period), and drives each of the blood pump P1, the liquid delivery pumps P2, P3, and stops the liquid delivery pump P4. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the dialyzer 2 and the arterial blood circuit 1a, and thus hemodiafiltration treatment (treatment in which dialysis (diffusion) and filtration are performed concurrently) accompanied by pre-dilution is performed.

Furthermore, in the case where hemodiafiltration treatment is selected, when pre and post-dilution is selected, the control unit 5 alternately achieves the state of (a) of FIG. 5 and the state of (b) of FIG. 5 (switches between closing and opening at a predetermined period), and drives each of the blood pump P1, the liquid delivery pumps P2, P3, P4. At this point, when the flow rate due to driving of the liquid delivery pump P2 is Q1, the flow rate due to driving of the liquid delivery pump P4 is set to Q2 (where Q1>Q2>0), the flow rate due to driving of the liquid delivery pump P3 is set to Q1+Quf (where Q1>0, Quf≥0). With this, the dialysate in the storage bag B1 is introduced into the dialyzer 2, the arterial blood circuit 1a and the venous blood circuit 1b, and thus hemodiafiltration treatment (treatment in which dialysis (diffusion) and filtration are performed concurrently) accompanied by pre and post-dilution is performed.

According to the embodiment, the blood purification apparatus includes the second dialysate supply line L4 that branches from the upstream side of the branch point of the dialysate supply line L3 in the dialysate introduction line L1 and that is connected to the blood circuit and has a liquid delivery pump disposed at a midpoint, and the second dialysate supply line L4 and the dialysate supply line L3 are respectively connected to the arterial blood circuit 1a and the venous blood circuit 1b (the second dialysate supply line L4 is connected to the arterial blood circuit 1a, the dialysate supply line L3 is connected to the venous blood circuit 1b). Thus, selection from pre-dilution, post-dilution and pre and post-dilution in hemofiltration treatment (HF) and hemodiafiltration treatment (HDF) can be performed more easily and smoothly.

Next, a third embodiment according to the present invention will be described. Similarly to the first and second embodiments, a blood purification apparatus according to this embodiment is applied to a hemodialysis apparatus for extracorporeally circulating the blood of a patient to purify the blood, and as illustrated in FIG. 4, the blood purification apparatus mainly comprises: a blood circuit including an arterial blood circuit 1a and a venous blood circuit 1b; a dialyzer 2 (blood purification means) that is interposed between the arterial blood circuit 1a and the venous blood circuit 1b, and that purifies the blood which flows through the blood circuit; a blood pump P1 comprised of a peristaltic pump disposed in the arterial blood circuit 1a; a dialysate introduction line L1 and a dialysate discharge line L2; liquid delivery pumps P2, P3 respectively disposed in the dialysate introduction line L1 and the dialysate discharge line L2; a dialysate supply line L3 connected to the connecting portion c of the venous blood circuit 1b; a second dialysate supply line L4 in which a liquid delivery pump P4 is disposed at a midpoint; an input unit 4; and a control unit 5. It is to be noted that the same component as in the first embodiment is labeled with the same symbol, and a detailed description thereof is omitted.

The second dialysate supply line L4 branches from the upstream side (branch point d) of the branch point a of the dialysate supply line L3 in the dialysate introduction line L1 and is connected to the blood circuit (the connecting portion b of the arterial blood circuit 1a), and the second dialysate supply line L4 is comprised of a flow path in which the liquid delivery pump P4 is disposed at a midpoint. Similarly to the liquid delivery pumps P2, P3 (as well as the blood pump P1), the liquid delivery pump P4 is comprised of a peristaltic pump that delivers liquid by pressing and rubbing against a flexible tube that forms the flow path of the second dialysate supply line L4.

Thus, the dialysate supply line L3 is connected to the connecting portion c of the venous blood circuit 1b, and the second dialysate supply line L4 is connected to the connecting portion b of the arterial blood circuit 1a, and thus the dialysate in the storage bag B1 can be supplied to the venous blood circuit 1b (in other words, post-dilution is possible) via the dialysate supply line L3 and can be supplied to the arterial blood circuit 1a (in other words, pre-dilution is possible) via the second dialysate supply line L4.

Similarly to the second embodiment, the input unit 4 allows input to a hemodialysis apparatus by a medical professional such as a doctor, and it is possible to input a desired treatment out of hemodialysis treatment (HD), hemofiltration treatment (HF) and hemodiafiltration treatment (HDF), and when hemofiltration treatment (HF) and hemodiafiltration treatment (HDF) are inputted, it is possible to select from pre-dilution in which dialysate (substitution solution) is injected into the upstream side (the arterial blood circuit 1a) of the dialyzer 2 (the blood purifier); post-dilution in which dialysate (substitution solution) is injected into the downstream side (the venous blood circuit 1b) of the dialyzer 2; and pre and post-dilution in which dialysate (substitution solution) is injected into both the upstream side and downstream side (the arterial blood circuit 1a and the venous blood circuit 1b) of the dialyzer 2.

The control unit 5 is electrically connected to the blood pump P1, the liquid delivery pumps P2, P3, P4 and the valve means 3 to cause a treatment inputted by the input unit 4 to be performed. The control unit 5 is configured to operate the valve means 3 to allow any treatment to be performed selected from hemodialysis treatment in which the dialysate supply line L3 is closed while the dialysate introduction line L1 is opened, hemofiltration treatment in which the dialysate supply line L3 is opened while the dialysate introduction line L1 is closed, and hemodiafiltration treatment in which the dialysate introduction line L1 and the dialysate supply line L3 are closed or opened in any manner.

When hemodialysis treatment is selected, as illustrated in (a) of FIG. 5, the control unit 5 allows the movable unit 3a of the valve means 3 to cause the dialysate supply line L3 to assume a closed state and the dialysate introduction line L1 to assume an opened state, and drives each of the blood pump P1, the liquid delivery pumps P2, P3. It is to be noted that the liquid delivery pump P4 is set to a stopped state. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the dialyzer 2, and thus hemodialysis treatment is performed.

When hemofiltration treatment is selected, as illustrated in (b) of FIG. 5, the control unit 5 allows the movable unit 3a of the valve means 3 to cause the dialysate introduction line L1 to assume a closed state and the dialysate supply line L3 to assume an opened state, and drives each of the blood pump P1, the liquid delivery pumps P2, P3. When post-dilution is selected, the liquid delivery pump P4 is stopped and the liquid delivery pumps P2, P3 are driven. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the venous blood circuit 1b, and thus hemofiltration treatment accompanied by post-dilution is performed.

Also, in the case where hemofiltration treatment is selected, when pre-dilution is selected, in addition to the blood pump P1 and the liquid delivery pumps P2, P3, the liquid delivery pump P4 is driven. At this point, when the flow rate due to driving of the liquid delivery pump P2 is Q1, the flow rate due to driving of the liquid delivery pump P4 is set to Q1, the flow rate due to driving of the liquid delivery pump P3 is set to Q1+Quf (where Q1>0, Quf≥0). With this, the dialysate in the storage bag B1 is introduced into the arterial blood circuit 1a, and thus hemofiltration treatment accompanied by pre-dilution is performed.

Furthermore, in the case where hemofiltration treatment is selected, when pre and post-dilution is selected, in addition to the blood pump P1 and the liquid delivery pumps P2, P3, the liquid delivery pump P4 is driven. At this point, when the flow rate due to driving of the liquid delivery pump P2 is Q1, the flow rate due to driving of the liquid delivery pump P4 is set to Q2 (where Q1>Q2>0), the flow rate due to driving of the liquid delivery pump P3 is set to Q1+Quf (where Q1>0, Quf≥0). With this, the dialysate in the storage bag B1 is introduced into the arterial blood circuit 1a and the venous blood circuit 1b, and thus hemofiltration treatment accompanied by pre and post-dilution is performed.

In the case where hemodiafiltration treatment is selected, when pre-dilution is selected, as illustrated in (a) of FIG. 5, the control unit 5 allows the movable unit 3a of the valve means 3 to cause the dialysate supply line L3 to assume a closed state and the dialysate introduction line L1 to assume an opened state, and drives each of the blood pump P1, the liquid delivery pumps P2, P3, P4. At this point, when the flow rate due to driving of the liquid delivery pump P2 is Q1, the flow rate due to driving of the liquid delivery pump P4 is set to Q2 (where Q1>Q2>0), the flow rate due to driving of the liquid delivery pump P3 is set to Q1+Quf (where Q1>0, Quf≥0). With this, the dialysate in the storage bag B1 is introduced into the dialyzer 2 and the arterial blood circuit 1a, and thus hemodiafiltration treatment accompanied by pre-dilution is performed.

In the case where hemodiafiltration treatment is selected, when post-dilution is selected, the control unit 5 alternately achieves the state of (a) of FIG. 5 and the state of (b) of FIG. 5 (switches between closing and opening at a predetermined period), and drives each of the blood pump P1, the liquid delivery pumps P2, P3, and stops the liquid delivery pump P4. At this point, when the flow rate due to driving of the liquid delivery pump P2 is Q1, the flow rate due to driving of the liquid delivery pump P3 is set to Q1+Quf (where Q1>0, Quf≥0). With this, the dialysate in the storage bag B1 is introduced into the dialyzer 2 and the venous blood circuit 1b, and thus hemodiafiltration treatment accompanied by post-dilution is performed.

Furthermore, in the case where hemodiafiltration treatment is selected, when pre and post-dilution is selected, the control unit 5 alternately achieves the state of (a) of FIG. 5 and the state of (b) of FIG. 5 (switches between closing and opening at a predetermined period), and drives each of the blood pump P1, the liquid delivery pumps P2, P3, P4. At this point, when the flow rate due to driving of the liquid delivery pump P2 is Q1, the flow rate due to driving of the liquid delivery pump P4 is set to Q2 (where Q1>Q2>0), the flow rate due to driving of the liquid delivery pump P3 is set to Q1+Quf (where Q1>0, Quf≥0). With this, the dialysate in the storage bag B1 is introduced into the dialyzer 2, the arterial blood circuit 1a and the venous blood circuit 1b, and thus hemodiafiltration treatment accompanied by pre and post-dilution is performed.

According to the embodiment, the blood purification apparatus includes the second dialysate supply line L4 that branches from the upstream side of the branch point of the dialysate supply line L3 in the dialysate introduction line L1 and that is connected to the blood circuit and has a liquid delivery pump disposed at a midpoint, and the second dialysate supply line L4 and the dialysate supply line L3 are respectively connected to the arterial blood circuit 1a and the venous blood circuit 1b (the second dialysate supply line L4 is connected to the arterial blood circuit 1a, the dialysate supply line L3 is connected to the venous blood circuit 1b). Thus, selection from pre-dilution, post-dilution and pre and post-dilution in hemofiltration treatment (HF) and hemodiafiltration treatment (HDF) can be performed more easily and smoothly.

Although the embodiments have been described so far, the present invention is not limited to these, and for instance, in addition to hemodialysis treatment (HD), hemofiltration treatment (HF), and hemodiafiltration treatment (HDF), other treatments different from those treatments may be selectable. Also, the valve means 3 is not necessarily to have the single movable unit 3a that is disposed to straddle the dialysate introduction line L1 and the dialysate supply line L3, and may provide separate valve means (such as electromagnetic valves) that are capable of closing and opening the dialysate introduction line L1 and the dialysate supply line L3 in any manner. It is to be noted that the blood purification treatment to which the invention is applied is not limited to dialysis treatment, and may be other treatment in which the blood of a patient is extracorporeally circulated to purify the blood.

Other functions may be added to the blood purification apparatus as long as the apparatus allows any treatment to be performed selected from hemodialysis treatment in which the dialysate supply line is closed while the dialysate introduction line is opened, hemofiltration treatment in which the dialysate supply line is opened while the dialysate introduction line is closed, and hemodiafiltration treatment in which hemodialysis and hemofiltration can be performed concurrently by alternately closing and opening the dialysate introduction line and the dialysate supply line.

REFERENCE SIGN LIST

1a Arterial blood circuit
1b Venous blood circuit
2 Dialyzer (blood purifier)
3 Valve means
4 Input unit
5 Control unit
L1 Dialysate introduction line
L2 Dialysate discharge line
L3 Dialysate supply line
L4 Second dialysate supply line
P1 Blood pump
P2 to P4 Liquid delivery pump

The invention claimed is:
1. A blood purification apparatus comprising:
a blood circuit that includes an arterial blood circuit and a venous blood circuit, and that is capable of extracorporeally circulating blood of a patient from a leading end of the arterial blood circuit to a leading end of the venous blood circuit;
a blood purification means that is interposed between the arterial blood circuit and the venous blood circuit of the blood circuit, and purifies blood that flows through the blood circuit;
a blood pump disposed in the arterial blood circuit;
a dialysate introduction line for introducing dialysate to the blood purification means, and a dialysate discharge line for discharging the dialysate from the blood purification means;
a liquid delivery pump disposed in the dialysate introduction line;
a dialysate supply line that branches from a downstream side of the liquid delivery pump in the dialysate introduction line and is connected to a predetermined portion of the blood circuit, and that supplies the dialysate of the dialysate introduction line to the blood circuit;
a valve means having a first opposing wall and a second opposing wall, the valve means closes and opens the dialysate introduction line and the dialysate supply line in any manner, the valve means comprising:
a movable unit positioned between the first opposing wall and the second opposing wall, wherein the dialysate introduction line is positioned between the movable unit and the first opposing wall and the dialysate supply line is positioned between the movable unit and the second opposing wall, and
an actuator that actuates the movable unit so that the movable unit closes the dialysate introduction line or the dialysate supply line by compressing the dialysate introduction line or the dialysate supply line between the movable unit and the first opposing wall or the second opposing wall respectively; and
a control unit that operates the valve means to allow hemodialysis treatment in which the dialysate supply line is closed while the dialysate introduction line is opened, hemofiltration treatment in which the dialysate supply line is opened while the dialysate introduction line is closed, and hemodiafiltration treatment in which the hemodialysis treatment and the hemofiltration treatment are performed concurrently by alternately closing and opening the dialysate introduction line and the dialysate supply line.

2. The blood purification apparatus according to claim 1, wherein the movable unit is disposed to straddle the dialysate introduction line and the dialysate supply line, and the movable unit is operable by the actuator to close one of the dialysate introduction line and the dialysate supply line and open the other as well as to close the other and open the one.

3. The blood purification apparatus according to claim 2, wherein when the hemodiafiltration treatment is selected, the valve means is capable of setting a time during which one of the dialysate introduction line and the dialysate supply line is closed and the other is opened, and a time during which the other is closed and the one is opened in any manner.

4. The blood purification apparatus according to claim 1, further comprising:
a second dialysate supply line that branches from an upstream side of a branch point of the dialysate supply line in the dialysate introduction line and is connected to the blood circuit, and a liquid delivery pump is disposed at a midpoint of the second dialysate supply line,
wherein the second dialysate supply line and the dialysate supply line are connected to each of the arterial blood circuit and the venous blood circuit.

5. The blood purification apparatus according to claim 1, wherein the liquid delivery pump is comprised of a peristaltic pump that delivers liquid by pressing and rubbing against a flexible tube that forms a flow path.

6. The blood purification apparatus according to claim 2, further comprising:
a second dialysate supply line that branches from an upstream side of a branch point of the dialysate supply line in the dialysate introduction line and is connected to the blood circuit, and a liquid delivery pump is disposed at a midpoint of the second dialysate supply line,
wherein the second dialysate supply line and the dialysate supply line are connected to each of the arterial blood circuit and the venous blood circuit.

7. The blood purification apparatus according to claim 3, further comprising:
a second dialysate supply line that branches from an upstream side of a branch point of the dialysate supply line in the dialysate introduction line and is connected to the blood circuit, and a liquid delivery pump is disposed at a midpoint of the second dialysate supply line,
wherein the second dialysate supply line and the dialysate supply line are connected to each of the arterial blood circuit and the venous blood circuit.

8. The blood purification apparatus according to claim 2, wherein the liquid delivery pump is comprised of a peristaltic pump that delivers liquid by pressing and rubbing against a flexible tube that forms a flow path.

9. The blood purification apparatus according to claim 3, wherein the liquid delivery pump is comprised of a peristaltic pump that delivers liquid by pressing and rubbing against a flexible tube that forms a flow path.

10. The blood purification apparatus according to claim 4, wherein the liquid delivery pump is comprised of a peristaltic pump that delivers liquid by pressing and rubbing against a flexible tube that forms a flow path.

11. The blood purification apparatus according to claim 7, wherein the liquid delivery pump is comprised of a peristaltic pump that delivers liquid by pressing and rubbing against a flexible tube that forms a flow path.

12. The blood purification apparatus according to claim 1, wherein as the movable unit compresses and closes the dialysate introduction line, the dialysate supply line is simultaneously decompressed and opened, or vice versa.

13. The blood purification apparatus according to claim 1, further comprising an input unit to select a desired treatment operation.

14. The blood purification apparatus according to claim 13, wherein the input unit is configured to further select from a pre-dilution in which the dialysate is injected into the arterial blood circuit, a post-dilution in which the dialysate is injected into the venous blood circuit, or a combination thereof in which the dialysate is injected into both the arterial blood circuit and the venous blood circuit.

15. The blood purification apparatus according to claim 1, wherein the control unit is electrically connected to the blood pump, the liquid delivery pump, and the valve means.

16. The blood purification apparatus according to claim 15, wherein the control unit drives each of the blood pump and the liquid delivery pump.

17. The blood purification apparatus according to claim 1, wherein the movable unit is a single movable unit.

18. The blood purification apparatus according to claim 1, wherein the valve means is an electromagnetic valve.

19. The blood purification apparatus according to claim 1, wherein the actuator is a motor secured to, or located within, the movable unit.

20. The blood purification apparatus according to claim 1, wherein the valve means includes a plurality of separate valves.

* * * * *